United States Patent [19]
Cho et al.

[11] Patent Number: 5,484,712
[45] Date of Patent: Jan. 16, 1996

[54] METHOD FOR PRODUCING ACLACINOMYCINS A, B, Y USING STREPOMYCES LAVENDOFOLIAE DKRS

[75] Inventors: Won T. Cho, Cheongju; Wan S. Kim, Seoul; Myung K. Kim, Seoul; Jin K. Park, Seoul; Hak R. Kim, Seoul; Sang K. Rhee, Seoul, all of Rep. of Korea; A. G. Domracheva, Moscow, Russian Federation; T. B. Panichkina, Moscow, Russian Federation; L. A. Saburoba, Moscow, Russian Federation; L. M. Nobikoba, Moscow, Russian Federation; Y. E. Bartochevichi, Moscow, Russian Federation

[73] Assignees: Dongkook Pharmaceutical Co. Ltd.; Ki Beom Kwon, both of Seoul, Rep. of Korea

[21] Appl. No.: 369,375

[22] Filed: Jan. 6, 1995

Related U.S. Application Data

[62] Division of Ser. No. 192,165, Feb. 4, 1994, Pat. No. 5,468,637.

[30] Foreign Application Priority Data

Sep. 3, 1993 [KR] Rep. of Korea .............. 93-17589

[51] Int. Cl.⁶ .............. C07H 17/04; C07H 15/244; C12N 1/20; C12P 19/56
[52] U.S. Cl. .............. 435/78; 435/252.35; 435/886; 536/6.4
[58] Field of Search .............. 435/252.35, 886; 424/78; 536/6.4

[56] References Cited

U.S. PATENT DOCUMENTS

| | | |
|---|---|---|
| 3,988,315 | 10/1976 | Umezawa et al. . |
| 4,204,038 | 5/1980 | Umezawa et al. .............. 435/78 |
| 4,209,588 | 6/1980 | Umezawa et al. .............. 435/886 |
| 4,337,312 | 6/1982 | Oki et al. .............. 435/78 |
| 4,383,037 | 5/1983 | Fujiwara et al. .............. 435/78 |
| 4,405,713 | 9/1983 | Fujiwara et al. .............. 435/78 |
| 4,471,052 | 9/1984 | Mitscher et al. .............. 435/886 |

OTHER PUBLICATIONS

ATCC *Catalogue of Bacteria and Bacteriophages*, 18th edition, Editors—Gherna et al., cover, copyright page and p. 335 (pub. 1992).

*Primary Examiner*—Herbert J. Lilling
*Attorney, Agent, or Firm*—Ratner & Prestia

[57] ABSTRACT

Disclosed herein are a novel strain of Streptomyces and a method for the production of aclacinomycins A, B, Y and aglycone thereof by cultivating the same. *Streptomyces lavendofoliae* DKRS(KCTC 0092BP) of the present invention is capable of producing aclacinomycins A, B, Y and aglycone with higher yield. Further, it is possible to selectively produce aclacinomycin A or Y by adjusting pH of the cultured broth of *Streptomyces lavendofoliae* DKRS to 4.4 or 4.6 with acetate buffer or hydrochloric acid, respectively.

6 Claims, No Drawings

METHOD FOR PRODUCING ACLACINOMYCINS A, B, Y USING STREPOMYCES LAVENDOFOLIAE DKRS

This application is a division of application Ser. No. 08/192,165, filed Feb. 4, 1994, now U.S. Pat. No. 5,468,637.

BACKGROUND OF THE INVENTION

1. Field of the Invention

The invention relates to a novel strain of the Streptomyces genus and a method for producing antitumor aclacinomycins A, B, Y and aglycones by cultivation of the strain.

2. Description of the Prior Art

Aclacinomycin are a group of anthracycline anti-tumor agents containing pyrrole and consists of three deoxypyranose residues. They exhibit cytotoxic activity by being intercalated into base pairs of DNA so that inhibiting synthesis of nucleic acid. Moreover, they selectively inhibit the synthesis of RNA unlike other anthracyclines such as daunorubicin, doxorubicin and carminomycin. Further, they are active against acute leukemia and malignant lymphoma while their cardiac toxicity is low.

Aclacinomycins may classified into three groups: aclacinomycins A, B and Y. They essentially have an aglycone residue, named as aklavine. Among them, aclacinomycin B had been scarcely employed in the clinics because it shows side effects and exhibits low antitumor activity. Aclacinomycin A has been practically employed due to its high anti-cancer or tumor activity low side effects and high yield of production. Aclacinomycin Y is expected to be the most useful anticancer agent since it shows considerably high antitumor activity and low side effects. However, its production yield from the culture broth of Streptomyces is low and it is required to improve the yield of the production.

A method for producing aclacinomycins by fermentation of *Streptomyces galilaeus* has been known (U.S. Pat. No. 3,988,315 to Hamao Umezawa). This patent reports that *Streptomyces galilaeus* produces about 18 analogues including aclacinomycins A, B and Y. However its production yield is very low: aclacinomycin A, a major product was produced in an amount of 46 mg/l culture broth, aclacinomycin B was produced in an mount of 23 mg/l and other products including aclacinomycin Y are produced in extremely small amounts. Accordingly, it is difficult to produce aclacinomycins in an industrial scale by using the above Streptomyces strain and there has been a need to provide a new strain which is capable of producing aclacinomycins in a high yield.

The present inventors had conducted extensive research to provide a process for producing aclacinomycins by fermentation in an industrial scale and as a result thereof had provided *Streptomyces lavendofoliae* 12/3A which is capable of producing aclacinomycins A and B. The present inventors made further researches for the purpose of providing an improved strain which produces larger amount of aclacinomycins and the purpose can be accomplished by the mutant *Streptomyces lavendofoliae* DKRS derived from the strain 12/3A.

SUMMARY OF THE INVENTION

This invention provides a new strain of *Streptomyces lavendofoliae* DKRS which is capable of producing a large quantity of aclacinomycins A, B, Y and aglycones thereof.

This invention also provides a method for producing aclacinomycins by cultivating the strain of *Streptomyces lavendofoliae* DKRS and recovering aclacinomycins from the broth and cells.

Still part of this invention is a method for selectively producing aclacinomycin A or Y by adjusting the pH of a culture broth to a certain value with acetate buffer or hydrochloric acid after cultivation of the strain of *Streptomyces lavendofoliae* DKRS.

DETAILED DESCRIPTION OF THE INVENTION

*Streptomyces lavendofoliae* 12/3A, which is the parent strain of *Streptomyces lavendofoliae* DKRS according to the invention, can produce 60 mg/l of aclacinomycin A and 10 mg/l of aclacinomycin B.

*Streptomyces lavendofoliae* DKRS of the invention can be obtained by mutaing the parent strain *Streptomyces lavendofoliae* 12/3A with a chemical mutagen, N-nitrosomethylbiuret(NMB). The mutant is capable of producing aclacinomycins A, B, Y and aglycones and particularly produces a large quantity of aclacinomycin Y.

The mutant of the invention, one of many that can be produced by the same method, was selected by following method. After cultivation of *Streptomyces lavendofoliae* 12/3A in a complete solid medium at 30° C. for 6–7 days, the spores were collected by filtration through a glass wool filter, washed three times with 0.05M Tris-malate buffer(pH 6.5) and diluted to a number of $1^6$–$10^8$ spores/ml with the same buffer. After adding NMB to the spore suspension to a final concentration of 500 µg/ml, the mixture was allowed to stand at 30° C. for 20 minutes. After completion of the reaction, spores were isolated by centrifugation or filtration, washed with sterile physilogical saline three times and streaked on the complete agar medium. After cultivation at 30° C. for 7–10 days, colonies of the mutant appeared on the agar plate.

The exemplary mutant, *Streptomyces lavendofoliae* DKRS of the invention had been deposited with Korean Collection for Type Cultures in Taejon, Korea on Aug. 26, 1993 and received an accesion number of KCTC 8539P. The deposit was converted into the deposit under the Budapest Treaty on Nov. 15, 1993 and received an accesion number of KCTC 0092BP.

A complete medium which may be employed in the invention has the following composition: glucose 10.%, casein hydrolysate 0.2%, meat extract 0.1%, yeast extract 0.1% and agar 1.5%, pH 7.0–7.2.

The strain *Streptomyces lavendofoliae* DKRS(KCTC 0092BP) according to the invention has the following microbiological properties:

1. Morphological properties

Under the microscope, when the strain is cultivated in a solid medium, substrate mycelia are not fragmented, and the spores are ellipsoidal and form moderately long chains. The spores are measured about 2.3 µm×1.4 µm and form oidia, and their surfaces are smooth.

2. Properties in various media

The exemplary strain of the invention shows the following properties when incubated at 28° C. in the following various solid media:

(1) On Waksman's medium, green growth; pink-brown soluble pigment.

(2) On Gaus-I medium, pink-white growth; red-brown substrate mycelium; no soluble pigment.

(3) On oatmeal medium, gray growth; red-brown substrate mycelium; no soluble pigment.

(4) On corn medium, dark brown growth; dark brown substrate mycelium.

(5) On Gaus-II medium, green-brown growth; dark brwon substrate mycelium; dark brwon soluble pigment.

(6) On soybean medium, light green growth; brown-green substrated mycelium; red-brown soluble pigment.

(7) On Riestrick's medium, brown growth; dark brown soluble pigment.

(8) On Czapek-Dock's medium, white-pink growth; red-brown substrate mycelium; no soluble pigment.

(9) On Bennet's medium, light-sandy growth; no soluble pigments.

(10) On meat-peptone agar, light sandy growth; brown soluble pigment.

(11) On glucose-asparagine medium, green growth; no soluble pigment.

3. Physiological properties

The exemplary strain of the invention is an aerobe and shows optimal growth at 28° C. It shows red-orange growth, peptonization, starch hydrolysis and gelatin liquefaction on a medium containing corn meal. It shows abundant growth with maltose and lactose; weak growth with rhamnose, xylose, arabinose and galactose; and no growth with sucrose, mannitol and sorbitol.

The differences in morphology and physiological properties between the parent strain and present strain are shown in Table 1.

TABLE 1

| | | *Streptomyces lavendofoliae* | |
|---|---|---|---|
| | | DKRS (Invention) | 12/3A (Parent) |
| I. | Morphology | | |
| | Sporangiophores | vertical to the basal mycelium and in the form of simple spirals size: 8.8–32 μm | vertical to the basal mycelium and in the form of simple spirals size: 10–12 μm |
| | Spore | rectangularly ellipsoidal size: 2.3 × 1.4 μm | nearly ellipsoidal size: 0.7 × 1.4 μm |
| | Sporulation | ++ | +++ |
| | Nucleoid | round or nearly ellipsoidal | sphere or nearly ellipsoidal |
| | Surface | smooth | smooth |
| | Oidia | oidia from substrate or aerial mycelium is rapidly developed and its size is variable | No |
| | Nucleoid | very large and filled in entire cell. | |
| II. | Physiological properties | | |
| | Peptonization | + | + |
| | Starch hydrolysis | + | + |
| | Gelatin liquefaction | + | + |
| | Utilization of carbohydrates[a] | | |
| | Maltose | +++ | ND |
| | Lactose | +++ | ND |
| | Rhamnose | + | + |
| | Glucose | + | +++ |
| | Fructose | ND | +++ |
| | Xylose | + | +++ |
| | Arabinose | + | +++ |
| | Galactose | + | +++ |
| | Sucrose | − | − |
| | Inositol | ND | +++ |
| | Mannitol | − | − |
| | Sorbitol | − | ND |

[a]+++: abundant growth
+: positive growth
−: no growth
ND: no detection

The method for the production of aclacinomycins by using the exemplary strain of the invention comprises the steps of cultivating *Streptomyces lavendofoliae* DKRS in a medium containing carbon sources, nitrogen sources and other nutrients, which are commonly employed in the fermentation of Streptomyces strains to accumulate aclacinomycins in the broth and inside the cells and of recovering them from the broth and cells.

The carbon sources employed in the cultivation of the invention may include, but is not intended to be limited thereto, starch and soybean meals. The nitrogen sources employed in the cultivation process of the invention may include, but is not intended to be limited thereto, soybean meals and ammonium sulfate. The inorganic components employed in the fermentation according to the invention may include, but is not intended to be limited thereto calcium carbonate, magnesium sulfate, zinc sulfate and sodium chloride.

The fermentation may be carried out under aerobic conditions at 28°–30° C., pH 7.2 for 4–5 days. Organic or inorganic alkaline materials, ammonia water and calcium carbonate may be used to adjust the pH during the fermentation.

Aclacinomycins may be separated from the broth or cells by using the conventional method for isolating low molecular materials, for example an extraction with organic solvents such as acetone or chloroform and column chromatography using silicic acid. A mixed solvent of toluene and isopropanol(30:1–35:1 by volume) is preferably employed for isolating or purifying aclacinomycins and aglycones.

In the present invention, aclacinomycins accumulated inside the cells may be extracted by using a mixture of methanol and chloroform(20:1) and analyzed by HPLC. For the HPLC, silica and a mixture of chloroform:methanol:acetic acid:water:triethanolamine(68:20:10:2:0.01(v/v)) may be employed as a stationary and mobile phases, respectively. The eluant is passed through the column at a flow rate of 1.0 ml/min and the collected fractions measured for their absorbance at 432 nm. The concentration of aclacinomycins A, B, Y and aglycones inside the cells may be calculated by comparing the absorbing residence time of authentic samples and that of those inside the cells.

According to the invention, aclacinomycin A is converted to Y and vice versa by changing the conditions of the isolation and purification steps. This conversion is likely due not only to the conditions of isolation but also to the enzymatic activity of the cells. Most of the aclacinomycin A contained in the culture broth and inside the cells is converted to aclacinomycin Y if the cultured broth is adjusted to pH 4.4 with acetate buffer while aclacinomycin Y is converted to aclacinomycin A if the culture broth is adjusted to pH 4.6 with hydrochloric acid. Accordingly, it is possible to selectively obtain aclacinomycin A or Y by adjusting the pH of the culture broth from which the product is recovered.

It has been confirmed by the inventors that purely isolated aclacinomycin Y showed higher anti-cancer activity against colon cancer and lower toxicity at even higher dose than those of aclacinomycins A or B.

The present invention shall be illustrated in more detail by way of the following Examples. The following Examples are merely illustrative and it should be understood that the present invention is not limited to these Examples.

EXAMPLES

Example 1:Cultivation of *S. lavendofoliae* TKRS and Parents Strain

A slant medium(Note 2) was inoculated with a platinum loopful of *Streptomyces lavendofoliae* DKRS, and incubation was carried out at 28° C. for 5 days. The thus obtained culture was inoculated into 50 ml of a seed culture medium(Note 3) in a 500 ml Sakaguchi-shaking flask, which previously had been adjusted to pH 7.8 and sterilized at 121° C. for 15 minutes. The incubation was carried out at 250 rpm for 2 days on a reciprocal shaker. A production medium-(Note 4) was adjusted to pH 7.5 and inoculated with the above seed culture to a concentration of 10% and fermentation was carried out at 28° C. for 4 days with agitation(500 rpm) and aeration(2.0 vvm).

The media employed in the present invention have the following compositions:

Note 2:Slant medium:starch 2%, $K_2HPO_4$ 0.05%, $MgSO_4$ 0.05%, $KNO_3$ 0.1%, salt 0.05%, $Fe_2(SO_4)_3$ 0.001%, agar 1.5–2% (pH 7.2).

Note 3:Seed culture medium:glucose 2%, starch 1.5%, soybean meal 1%, yeast extract 1%, $CaCO_3$ 0.3%, $MgSO_4$ 0.2%, NaCl 0.3% (pH 7.8).

Note 4:Production medium:glucose 3%, starch 3.5%, soy meal 1%, $CaCO_3$ 0.5%, $MgSO_4$ 0.2%, $FeSO_4$ 0.001%, $ZnSO_4$ 0.001% (pH 7.5).

The parent strain and mutant of the invention were cultivated by following the same procedure described above and the amounts of aclacinomycins produced in each culture broth were measured. The results are shown in Table 2.

TABLE 2

| Strains | Amount of aclacinomycins (mg/l) | | |
|---|---|---|---|
| | A | B | Y |
| Parent strain RS | 60 | 10 | — |
| Inventive DKRS | 60 | 70 | 90 |

As can be seen from Table 2, the strain DKRS, representative of the present invention, produces a large amount of aclacinomycin Y and shows an improved produciton of aclacinomycin B when compared with the parent strain RS and consequently is believed to be a mutant in which a part of the synthesis pathway of aclacinomycin as a secondary metabolite is altered.

Example 2:Isolation of Aclacinomycins

In this Example, aclacinomycins were isolated from the culture broth of *Streptomyces lavendofoliae* DKRS. The culture broth(700 ml) which was obtained in Example 1 was adjusted to pH 4.5 with hydrochloric acid and filtered to separate the mycelia from the broth. Chloroform was added to the mycelia to a concentration of 2 ml/g mycelia, and the mixture was well mixed for 1 hour and filtered. This procedure was repeated twice.

The chloroform filtrate(120 ml) was collected and concentrated in a vacuum evaporator. To the concentrate was added 15 ml of a mixed solvent of butyl acetate and acetone(4:1) and dissolved thoroughly therein. The resulting solution was treated with acetate buffer(pH 3.4) to extract products and reextracted with chloroform. After chloroform was evaporated and the extract was concentrated, n-hexane or petroleum ether were added to precipitate aclacinomycins A(27 mg), B(35 mg) and Y(41 mg).

Example 3:Separation of Aclacinomycins A, B, and Y from Broth at pH 4.6

The culture broth(700 ml) obtained in Example 1 was adjusted to pH 4.6 with hydrochloric acid and the mixture was mixed well at 28° C. for 3 hours. Then, the procedure in Example 2 was repeated to give aclacinomycins A(50 mg), B(20 mg) and Y(13 mg).

Example 4:Obtaining Aclacinomycins A, B at pH 4.4

The culture broth(700 ml) obtained in Example 1 was adjusted to pH 4.4 with acetate buffer and the mixture was mixed well at 28° C. for 2 hours. Then, the procedure in Example 2 was repeated to give aclacinomycins A(3 mg), B(40 mg) and Y(50 mg).

Example 5: Separating Aclacinomycins A, B, and Y from Broth and Mycelia by Solvent Extraction A fermentation medium(5 l) having the following composition[Note 5] was placed in a 10 l fermentor and adjusted to pH 7.5. A seed culture obtained in Example 1 was inoculated to a concentration of 10% and fermentation was carded out at 28° C. for 4 days under agitation(350 rpm) and aeration(1.0 vvm).

Note 5: Fermentation medium: glucose 3%, starch 5.5%, soy meal 1.5%, $CaCO_3$ 0.9%, $MgSO_4$ 0.25%, $ZnSO_4$ 0.002%, $FeSO_4$ 0.002%.

Thus obtained culture broth(3.5 l) contains aclacinomycins A(245 mg), B(315 mg) and Y(560 mg). The broth was adjusted to pH 4.6 with hydrochloric acid and centrifuged to give mycelia. To the mycelia was added 1.5 l of chloroform and mixed well for 1 hour. This procedure was repeated twice.

On the other hand, 600 ml of chloroform were added to the filtrate to extract aclacinomycins.

The thus obtained chloroform extracts were combined together and concentrated under vacuo. The precipitates were dissolved in a mixed solvent of buthyl acetate and acetone(4:1 by volume). The resulting solution was mixed with sodium sulfate and the mixture was filtered and concentrated. Finally, n-hexane was added to give precipitates and evaporated to give 1.5 g of mixed aclacinomycins.

Example 6: Purification of Aclacinomycins by Collumn Chromatography

The mixed aclacinomycins(1.5 g) obtained in Example 5 was dissolved in a minimum amount of mixed solvent of toluene and chloroform(8:2 by volume) and subjected to chromatography on a column packaged with silicic acid. As an eluant, toluene was employed. After fractions containing aglycones were eluted, the eluant was changed to a mixed solvent of toluene and isopropanol(35:1 by volume) to give fractions containing aclacinomycin B. Then a mixed solvent of toluene and isopropanol(30:1 by volume) was employed as an eluant to give fractions containing aclacinomycin Y.

To the fractions containing the products was added n-hexane or petroleum ether to precipitate the products and the precipitates were dried to give aglycones(10 mg), and aclacinomycin B(154 mg), Y(182 mg) and A(75 mg), all of which were in the form of yellow powder.

What is claimed is:

1. A method for producing aclacinomycine A, B and Y, comprising growing a pure cell culture of *S. lavendosoliae* DKRS having the ATCC Accession No. KCTC 0092BP in an expression medium at a temperature of about 28° to 30° C. and a pH of about 6.8 to 7.5 under aerobic conditions;

allowing the formation of aclacinomycins A, B and Y in the cell and the medium; and separating the aclacinomycine from the medium and the cells.

2. The method of claim 1, wherein the aclacinomycins A, B and Y are separated from the cells and the medium by extraction with a solvent mixture comprising toluene and isopropanol in a proportion of about 30:1 to 35:1 (v:v).

3. A method of selectively producing aclacinomycin Y, comprising growing a pure cell culture of *S. lavendosoliae* DKRS having the ATCC Accession No. KCTC 0092BP in an expression medium at a temperature of about 28° to 30° C. and a pH of about 6.8 to 7.5 under aerobic conditions;

allowing the formation of aclacinomycins A, B and Y in the cell and the medium;

adjusting the pH of the medium to about 4.4; and separating aclacinomycin Y from the medium and the cells.

4. The method of claim 1, wherein the pH of the medium is adjusted with an acetate buffer.

5. A method of selectively producing aclacinomycin A, comprising;

growing a pure cell culture of *S. lavendosoliae* DKRS having the ATCC Accession No. KCTC 0092BP in an expression medium at a temperature of about 28° to 30° C. and a pH of about 6.8 to 7.5 under aerobic conditions;

allowing the formation of aclacinomycins A, B and Y in the cell and the medium;

adjusting the pH of the medium to about 4.6; and separating aclacinomycin A from the medium and the cells.

6. The method of claim 5, wherein the pH is adjusted with hydrochloric acid.

* * * * *